(12) United States Patent
Carter et al.

(10) Patent No.: US 7,338,530 B2
(45) Date of Patent: Mar. 4, 2008

(54) STENT

(75) Inventors: Frank Carter, Wormleysburg, PA (US); Anthony Kalloo, Glenn Dale, MD (US); P. Jay Pasricha, Houston, TX (US)

(73) Assignee: Checkmed Systems, Inc., Camp Hill, PA (US)

( * ) Notice: Subject to any disclaimer, the term of this patent is extended or adjusted under 35 U.S.C. 154(b) by 0 days.

(21) Appl. No.: 10/719,066

(22) Filed: Nov. 24, 2003

(65) Prior Publication Data

US 2005/0113933 A1    May 26, 2005

(51) Int. Cl.
*A61F 2/04* (2006.01)

(52) U.S. Cl. .................................... 623/23.66

(58) Field of Classification Search ............ 623/23.64, 623/1.13, 1.15, 1.25, 1.11, 1.12, 1.23, 1.38; 604/8, 93.01, 94.01
See application file for complete search history.

(56) References Cited

U.S. PATENT DOCUMENTS

| | | | | |
|---|---|---|---|---|
| 3,123,077 A | * | 3/1964 | Alcamo | 606/228 |
| 3,821,956 A | | 7/1974 | Gordhamer | |
| 4,307,723 A | * | 12/1981 | Finney | 604/8 |
| 4,350,169 A | | 9/1982 | Dutcher et al. | |
| 4,459,318 A | | 7/1984 | Hyans | |
| 4,521,210 A | | 6/1985 | Wong | |
| 4,550,447 A | | 11/1985 | Seiler, Jr. et al. | |
| 4,677,143 A | | 6/1987 | Laurin et al. | |
| 4,699,611 A | | 10/1987 | Bowden | |
| 4,790,810 A | * | 12/1988 | Pugh et al. | 604/8 |
| 4,795,439 A | | 1/1989 | Guest | |
| 4,813,925 A | | 3/1989 | Anderson | |
| 4,846,791 A | | 7/1989 | Hattler et al. | |
| 4,950,228 A | * | 8/1990 | Knapp et al. | 604/8 |
| 4,973,301 A | | 11/1990 | Nissenkorn | |
| 5,052,998 A | * | 10/1991 | Zimmon | 604/8 |
| 5,167,614 A | | 12/1992 | Tessmann | |
| 5,176,626 A | | 1/1993 | Soehendra | |
| 5,246,445 A | | 9/1993 | Yachia | |
| 5,486,191 A | | 1/1996 | Pasricha et al. | |
| 5,522,881 A | * | 6/1996 | Lentz | 623/1.13 |
| 5,607,464 A | | 3/1997 | Trescony et al. | |
| 5,628,786 A | | 5/1997 | Banas et al. | |
| 5,653,745 A | | 8/1997 | Trescony et al. | |
| 5,776,160 A | | 7/1998 | Pasricha et al. | |

(Continued)

FOREIGN PATENT DOCUMENTS

DE    88138    8/1896

(Continued)

*Primary Examiner*—Alvin J. Stewart
(74) *Attorney, Agent, or Firm*—Barnes & Thornburg LLP (57) ABSTRACT

A biliary stent has a number of smooth-surfaced wings extending radially outwardly from a central region and extending longitudinally along substantially the entire length of the stent. A securement barb is located at one end of the stent and extends generally radially outwardly toward a side of the stent in cantilevered fashion at an angle less than or equal to 90°. The securement barb is angled such that it presents an outward-facing half-arrowhead profile. At least one end of the stent is smoothly or conically tapered. In one embodiment, the wings extend linearly along the stent; in another embodiment, the wings extend helically along the stent. Either embodiment may have a pigtail configuration at one or both ends.

36 Claims, 8 Drawing Sheets

U.S. PATENT DOCUMENTS

| | | | |
|---|---|---|---|
| 5,855,597 A * | 1/1999 | Jayaraman | 623/1.16 |
| 5,989,207 A * | 11/1999 | Hughes | 604/8 |
| 6,124,523 A | 9/2000 | Banas et al. | |
| 6,132,471 A | 10/2000 | Johlin, Jr. | |
| 6,214,037 B1 * | 4/2001 | Mitchell et al. | 623/1.11 |
| 6,221,060 B1 * | 4/2001 | Willard | 604/264 |
| 6,322,585 B1 | 11/2001 | Khosravi et al. | |
| 6,325,820 B1 | 12/2001 | Khosravi et al. | |
| 6,332,892 B1 * | 12/2001 | Desmond et al. | 623/1.15 |
| 6,383,171 B1 * | 5/2002 | Gifford et al. | 604/508 |
| 6,692,504 B2 * | 2/2004 | Kurz et al. | 606/127 |
| 6,767,339 B2 * | 7/2004 | Reydel | 604/175 |
| 2001/0041929 A1 | 11/2001 | Oepen | |
| 2001/0051823 A1 | 12/2001 | Khosravi et al. | |
| 2002/0032479 A1 | 3/2002 | Hankh et al. | |
| 2002/0038142 A1 | 3/2002 | Khosravi et al. | |
| 2003/0093145 A1 | 5/2003 | Lawrence-Brown et al. | |
| 2003/0100859 A1 | 5/2003 | Henderson et al. | |
| 2003/0120331 A1 * | 6/2003 | Chobotov et al. | 623/1.13 |

FOREIGN PATENT DOCUMENTS

| | | |
|---|---|---|
| DE | 7608671 | 7/1976 |
| EP | 0 059 620 | 9/1982 |
| EP | 0141006 | 1/1984 |
| FR | 564832 | 1/1924 |
| GB | 105038 | 3/1917 |
| GB | 189127 | 5/1923 |
| JP | 2000316979 | 11/2000 |
| SU | 1641356 A1 | 4/1991 |
| SU | 1715364 | 2/1992 |
| SU | 1759431 | 9/1992 |

* cited by examiner

STENT

FIELD OF THE INVENTION

The invention relates to stents that can be used to maintain flow of fluid in otherwise blocked ducts in the body. More particularly, the invention relates to stents used to facilitate drainage from a patient's common bile duct and/or pancreatic duct in medical instances where the patient's bile duct or pancreatic duct is obstructed due, for example, to biliary or pancreatic cancer or other disease, whether benign or malignant.

BACKGROUND OF THE INVENTION

Biliary and pancreatic cancers often are diagnosed when the patient presents specific symptoms characteristic of a blockage of either the patient's bile and/or pancreatic duct. In the case of a biliary cancer, the symptoms often include jaundice. Unfortunately, by the time such a stage of either disease is reached, the tumor is usually at an advanced stage and, therefore, is inoperable. Accordingly, management of the disease at this stage usually consists of palliation only.

Although surgical bypass procedures can be effective for palliation, most patients presenting with biliary or pancreatic cancer are either too sick to undergo major bypass surgery or have too short a remaining life-span to make such duct bypass surgery advisable. Therefore, palliation of jaundice or other symptoms associated with biliary or pancreatic cancer is most often accomplished using an endoscopically inserted stent or endoprosthesis that is positioned to bridge the obstructed area, i.e., so as to maintain a fluid flow pathway across (or past) the obstruction.

The prior art includes several examples of stents that have been and continue to be employed during endoscopic procedures so that flow of biological fluids may be reasserted in a patient. Generally, there are two types of stents that are typically employed: 1) plastic and 2) metal. Conventional plastic stents, formed in the shape of a cylinder, have a tendency to clog with debris and form a biofilm early in their use, which means that these stents have a limited operational lifetime. Conventional metal stents provide an improved operational lifetime over plastic stents because they are designed with a larger initial lumen. However, metal stents are often many times more expensive than plastic stents. In addition, since metal stents, like their plastic counterparts, are tubular in design, they also have a tendency to clog during their operational lifetimes. Moreover, metal stents are technically more difficult to insert into the patient and, once in place, cannot be removed.

Specific designs for stents and drains are known in the art. Several examples of known stents and drains are discussed below.

U.S. Pat. Nos. 5,486,191 and 5,776,160 both describe a winged biliary stent that has a central wire stylet lumen 18 surrounded by a core and several, grooved wings 14. Each wing 14 has a width that is substantially larger than the width of the core. The wings 14 may be disposed around the core in a helical fashion, if desired. Rather than discharge biological flow through a lumen through the center of the device, these stents permit flow across the exterior surfaces of the grooved wings 14.

French Patent No. 564,832 illustrates a surgical drain. The surgical drain has a large opening that passes through its center. The surface of the drain includes helically-disposed surface protrusions.

German Patent No. 88138 illustrates a wound drain that has a plus-shaped cross-section. It appears that there is a small hole passing through the longitudinal center of the device. Moreover, it also appears that there are a number of semicircular holes passing laterally through the four radial extensions. One end of the drain includes a protrusion, labeled "d."

British Patent No. 105,038 also describes a surgical drain with a plus-shaped cross-section. As the patent describes, by allowing the patient's tissue to form the walls of the drain, the tissue's normal undulations assist in the drainage of fluid from the wound. One embodiment of the drain described includes three arms extending outwardly from a central core through which is provided a central opening or passage.

European Patent No. 0 059 620 describes a wound drain catheter with a plurality of strut portions 32 capped with overhang portions 34. The drain is designed to be inserted into a wound and to be connected to a vacuum source to pull fluids from the wound.

U.S. Pat. No. 4,307,723 describes a urethral stent 10 with a central lumen 23 and several grooves 17 in the stent 10. The stent 10 includes hooked ends 13, 14, which are commonly referred to as "pig tails" in the stent art. Pig tails help hold the stent in position, after the stent has been placed within the patient.

British Patent No. 189,127 describes a wound drainage plug with a central duct E from which several ribs B extend. The ribs B form triangular grooves A around the periphery of the wound drain. The drain preferably is made of India rubber.

Soviet Patent No. 1641356 appears to illustrate a drain with a plurality of ribs extending outwardly from a central portion. The ribs appear to be helically disposed around the drain.

U.S. Pat. No. 6,132,471 describes a stent for draining the pancreatic and biliary ducts. The stent 20 is made from a soft, biocompatible material. The stent is tubular in shape with a smooth, continuous outer surface and an internal lumen 25, 45. The distal end portion 30 of the stent 20 is formed into a conical or tapered shape 40. The proximal end 35 of the stent 20 does not include a tapered section 40.

U.S. Patent Application Publication No. 2001/0041929 describes a stent 1 that is designed for placement in narrow portions of hollow vessels within the human body. The stent is essentially a cylindrical body with a central channel permitting fluid to pass therethrough. The stent body 2 is made of a flexible web material, even though it is illustrated as a solid, cylindrical tube. The first and second end portions 3, 4 have wall thicknesses $W_{E1}$ and $W_{E2}$ that are smaller than the wall thickness $W_H$ of the central portion 5. As the patent discusses, the differing wall thicknesses alter the flexibility of the stent 1 by comparison with a stent that does not include this feature.

U.S. Patent Application Publication No. 2003/0100859 describes an arterio-venous shunt graft 10. The shunt graft 10 has a main body 12 with an arterial end 14 and a venous end 16. The main body 12 may have a tapered portion 20 adjacent to the arterial end 14. A plurality of ribs 22 are formed on the exterior of the main body 12.

U.S. Pat. No. 6,124,523 describes an encapsulated stent 200 that is radially expandable. The stent 200 has a central passage or lumen 28 passing therethrough. The stent 200 includes opposing ends 216, 218 that flare radially outwardly after the stent is radially enlarged. Barbs 213 are formed on the second tubular member 214 (the outer member) to assist in fixation of the device, once expanded.

While adequate for the medical procedures described in each of the references discussed above, the prior art fails to provide a design for a stent that is simple to manufacture, may be easily inserted into the biliary or pancreatic tract of a patient, and includes one or more securement features so that it resists the tendency to migrate within the patient, even if emplaced within the patient for an extended period of time.

BRIEF SUMMARY OF THE INVENTION

Accordingly, one aspect of the present invention is to provide a stent that is manufactured from plastic.

Another aspect of the present invention is to provide a stent that does not need to be manually expanded, once inserted into the patient's common bile duct or pancreatic duct.

Still another aspect of the present invention provides a stent that may be inserted into a patient using a guide wire, such as used during an endoscopic surgical procedure.

A further aspect of the invention provides a winged stent that establishes a fluid pathway past an obstruction in the common bile duct or pancreatic duct without relying on a central lumen, which may become obstructed by biological materials during its operational lifetime.

The present invention features a stent that, in certain respects, is easier to manufacture and is easier to emplace within a patient than prior art stents, and that has securement barbs that facilitate retention of the stent within the patient.

A stent according to the invention has a number of smooth-surfaced wings extending radially outwardly and longitudinally along substantially the length of the stent, with at least one securement barb disposed adjacent to one end of the stent. The securement barb has a barb root and a barb tip, with the barb root securing the securement barb to the body of the stent. The securement barb extends generally radially outwardly from the stent body in cantilevered fashion from the barb root to the barb tip. The barb root is preferably located nearer to the end of the stent body than the barb tip, thus giving the end of the stent a half-arrowhead profile.

In exemplary embodiments of the invention, the securement barb tapers in width from the root to the tip, and the root extends circumferentially approximately half way around the stent body. This gives the securement barb a generally teardrop shape when viewed end-on, which helps secure the stent within the common bile duct or pancreatic duct.

The stent may also have one or more conically tapered tip portions, with the tip portion being disposed at one or both ends of the stent body. The securement barb extends from the tip portion. Preferably, the tip portion extends from a transition region on the body, which is a region where the radial height of the wings decreases toward the end of the stent body.

The wings of the stent are disposed substantially parallel to one another. In one configuration, the wings extend linearly along the body. In another configuration, they extend helically along the body.

The wings may taper in thickness from their roots to their tips, or they make have a constant thickness.

Preferably, the tips of the wings are rounded or blunted slightly, to minimize or avoid patient discomfort. Blunted tips also help to avoid laceration of, perforation of, damage to, and/or inflammation of the common bile duct or pancreatic duct to minimize potentially adverse reactions when emplaced within a patient.

The stent may also have a lumen defined within the body, the lumen extending through the body between the two ends thereof and being constructed and arranged to accommodate a guide wire therein for implantation within the patient.

Alternatively, the stent can be formed with a solid body, in which case it would be inserted simply by being pushed along a canula.

Preferably, the stent according to the invention is made from Pellethane™, which is a trademark of the Dow Chemical Company for a broad product family of thermoplastic polyurethane elastomers.

Additionally, the stent manufactured according to the invention may include a design where at least one of the ends of the stent preferably has what is referred to in the art as a "pig tail" configuration to enhance retention of the stent within the biliary or pancreatic duct.

Other aspects of the invention will be made apparent from the description that follows and from the drawings appended hereto.

BRIEF DESCRIPTION OF THE DRAWINGS

The invention will now be described in greater detail in connection with the attached drawings, in which.

DETAILED DESCRIPTION OF THE INVENTION

A first embodiment of a stent 10 according to the invention is illustrated in FIGS. 1–5. The stent 10 is generally elongated and is sized to fit within a human's biliary or pancreatic duct. While the stent 10 of the present invention is intended for use in the common bile duct or pancreatic duct of a patient having a ductal occlusion or obstruction, the stent 10 may be used in other areas within the human body. Therefore, while the instant description focuses primarily on biliary and pancreatic ductal uses, the potential areas of use are not intended to be limited thereby. As would be appreciated by those skilled in the art, the stent 10 may find application to various arterial and venous obstructions or occlusions. Moreover, the stent 10 may be employed in other channels within the human body. In addition, the stent 10 is not limited solely to use in humans.

Having been designed for biliary or pancreatic use, the stent 10 preferably has a length L that is on the order of 12.0 cm and a cross-sectional width W that is on the order of 0.4 cm. As would be appreciated by those skilled in the art, however, the dimensions for the length L and width W are exemplary only. It is contemplated that the length L of the stent 10 may be made longer or shorter depending upon the particular needs for a specific patient and the location where the stent 10 is emplaced. Similarly, the width W also may be increased or decreased to accommodate the specific needs of the patient and the location where the stent 10 is emplaced.

The stent 10 has a main or central body portion 12 that extends substantially along the entire length of the stent 10, from one end 14 to the other end 16. The stent 10 has a plurality of rib-like wings 18 that extend radially from the main or central body portion 12, substantially along the entire length L thereof. In this embodiment, the wings extend linearly from one end 14 to the other end 16 of the stent 10. Preferably, the rib-like wings 18 present a smooth surface throughout their entire length on the central body portion 12. Of course, as would be appreciated by those skilled in the art, the surfaces of the wings 18 may be grooved, as described in U.S. Pat. Nos. 5,486,191 and 5,776,160, the contents of both of which are incorporated herein by reference. Moreover, it is contemplated that the wings 18 may be grooved along only a portion of their length but be smooth along another portion. Also, it is contemplated that some of the wings 18 may be grooved while others of the wings 18 present a smooth surface.

In the preferred embodiment of the stent 10, there are six wings that extend outwardly from the central body portion 12. As would be appreciated by those skilled in the art, a greater or fewer number may be used without deviating form the scope of the present invention. In particular, it is contemplated that the stent 10 might have 3, 4, or 5 wings. It is also contemplated that the stent 10 could be provided with 7 or 8 wings (or more), as needed. FIG. 5 provides a cross-sectional end view of one variant of the stent 10 shown in FIG. 1. In FIG. 5, only three wings 18 are employed, rather than the six wings 18 shown in FIG. 4.

With respect to the number of wings 18 employed, it is contemplated that the three is the smallest number of wings 18 that may be employed to keep open the biliary or pancreatic duct. The largest number of wings 18 has not been determined. However, it is believed that the addition of wings 18 beyond a maximum number will inhibit biliary or pancreatic flow. Therefore, there is an upper limit to the number of wings 18 that may be provided. Factors that will contribute to the maximum permissible number of wings 18 include the shape of the wings 18, their thicknesses, and their ability to be spaced around the central core, among others.

Figure 4:
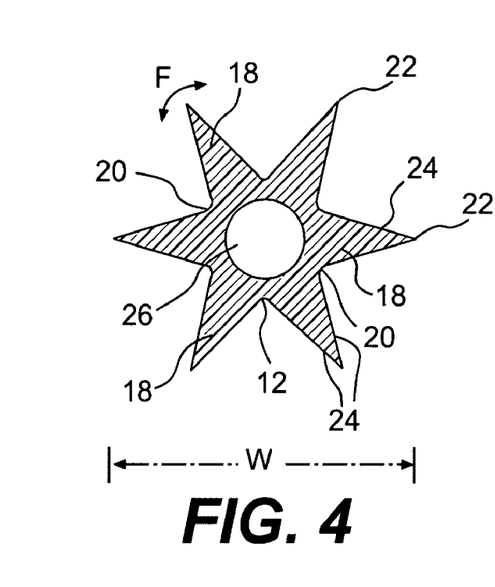
FIG. 4 is a cross-sectional end view of the embodiment illustrated in FIG. 1, the view being taken along the line 4—4 in FIG. 1.
Figure 5:
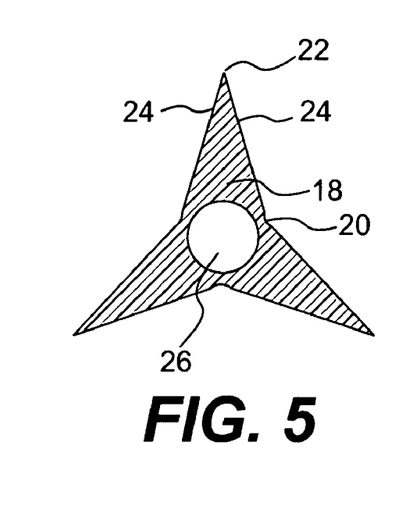
FIG. 5 is a cross-sectional end view of one variant of the embodiment illustrated in FIG. 1.

Preferably, the wings 18 taper downwardly in thickness from their roots 20 to their radially outer edges 22, as best illustrated in FIGS. 4 and 5. Such a configuration provides the wings 18 with sufficient lateral rigidity (i.e., rigidity to resist flexure from side-to-side as illustrated by double-headed arrow F in FIG. 4) to hold open the duct into which the stent 10 is placed. Alternatively, depending, for example, on the stiffness or rigidity of the material from which the stent 10 is fabricated, the wings 18 may have a uniform width or thickness from their roots 20 to their radially outer edges 22.

As illustrated, the wings 18 each have preferably a triangular cross-section. As indicated, this is but one possible construction. It is contemplated that each wing 18 alternatively may have a rectangular cross-section. In these two examples, it is contemplated that the surfaces of the wings 18 are planar. However, the surfaces may also be curved. For example, the wings may present an convex (or concave) parabolic surface, which may facilitate biological flow.

In the various figures, the radially outer edges (or tips) 22 of the wings 18 are shown with a "sharp" edge. In other words, the radially outer edges 22 are formed by the intersection of the two planar surfaces that define the surface of the wings 18. While it is not contemplated that the "sharp" radially outer edges 22 of the wings 18 will present any difficulties in the patient, especially because stent 10 is preferably made from a pliable plastic material, it is contemplated that the radially outer edges 22 of the wings 18 might present surfaces that irritate or inflame the interior surfaces of the biliary or pancreatic duct. As a result, the radial outer edges 22 of the wings 18 preferably are rounded or blunted slightly to minimize discomfort to the patient and avoid laceration or inflammation of the biliary or pancreatic duct tissue.

The surfaces 24 of the wings 18 preferably are smooth for ease of manufacturing, i.e., to simplify making the extrusion dies used to make the stent 10 according to the invention. Although not required to practice the invention, the wings 18 preferably are uniformly or equiangularly spaced circumferentially around the main or central body portion 12. A small-diameter guidewire lumen 26 extends centrally along the entire length of the stent 10, i.e., from one tip 28 of the stent 10 to the other tip 30. The guidewire lumen 26 is on the order of 1 mm in diameter and allows the stent 10 to be moved into proper position by being pushed along a guidewire, as is known in the art.

Naturally, as would be appreciated by those skilled in the art, a 1 mm diameter lumen 26 is not the only size contemplated to fall within the scope of the present invention. To the contrary, any suitable diameter lumen 26 may be employed. Moreover, it may be desirable to have a lumen 26 with a sufficiently large diameter to permit some flow of bile (or other fluid) therethrough, even though such a construction is not preferred for the present invention. It is contemplated that most of (if not all) of the biological flow will occur between the wings 18 of the stent 10 and not through the central lumen 26.

Although the stent 10 is illustrated as having a distinct central body portion 12 from which the wings 18 extend, with the guidewire lumen 26 positioned centrally within and extending longitudinally along the length of the main or central body portion 12, it should be appreciated that it is not strictly necessary to have such a distinct main or central body portion 12. For example, depending on the thickness of the wings 18, the cross-section of the stent 10 may be shaped more like an asterisk (*), with the wings 18 joined to each other and extending from a central juncture region of the asterisk and with the guidewire lumen 26 extending centrally along the length of that central juncture region. In other words, wings 18 connect at their roots 20 to one another to form the central portion 12 and the lumen 26.

As further illustrated in FIGS. 1–5, the stent 10 according to the invention is preferably tapered and barbed at each end 14, 16. In particular, each end 14, 16 has a transition region 32, 34, where the radial height of the wings 18 decreases, and a smooth-surfaced, preferably conically tapered tip portion 36, 38. The smooth, conically tapered tip portions 36, 38 cooperate with the transition regions 32, 34 to present a gradual transition from the tips 28, 30 to the central body portion 12 of the stent 10. This facilitates placement of the stent 10 in the patient's biliary or pancreatic tract, because, among other reasons, the gradual transition helps guide the stent 10 around the biliary or pancreatic obstruction.

Figure 1:
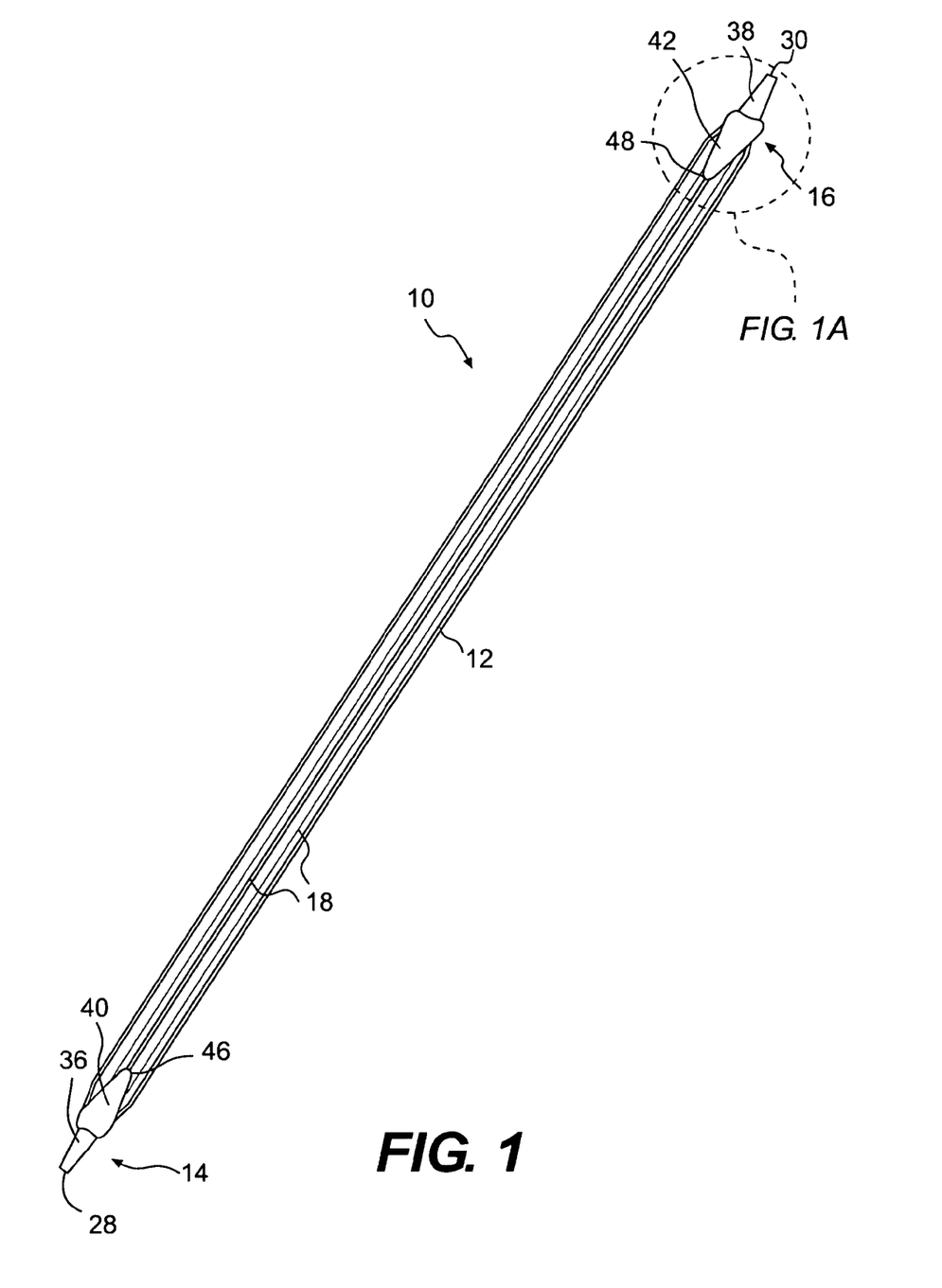
FIG. 1 is a perspective view of one embodiment of the stent of the present invention.
Figure 1A:
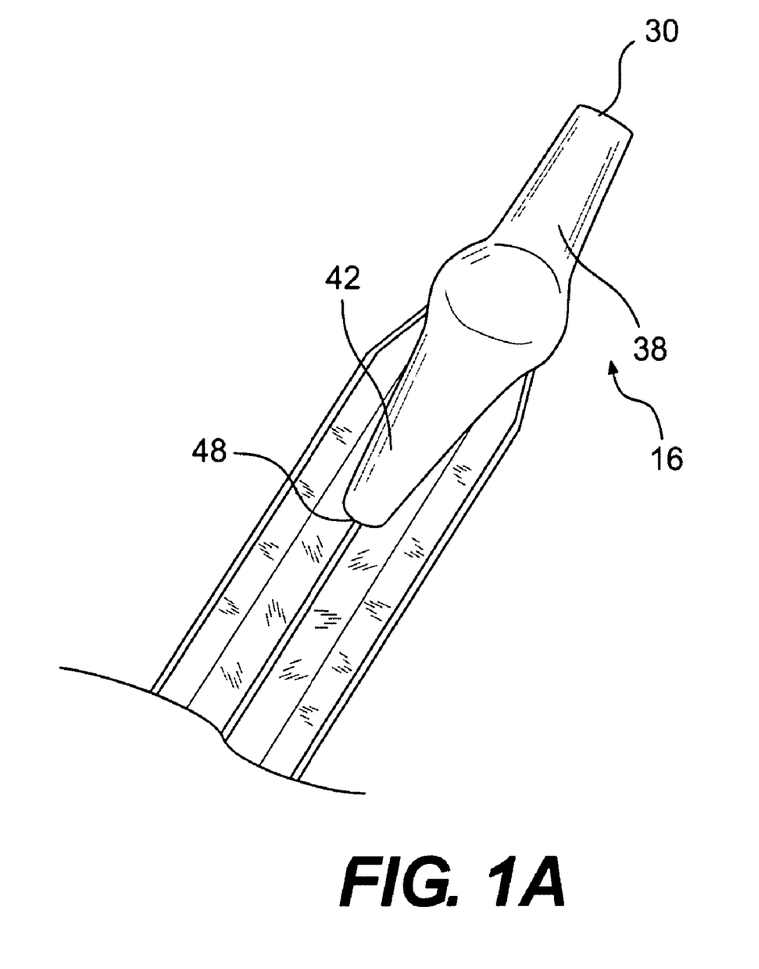
FIG. 1A is an enlarged view of one end of the stent depicted in FIG. 1.
Figure 6:
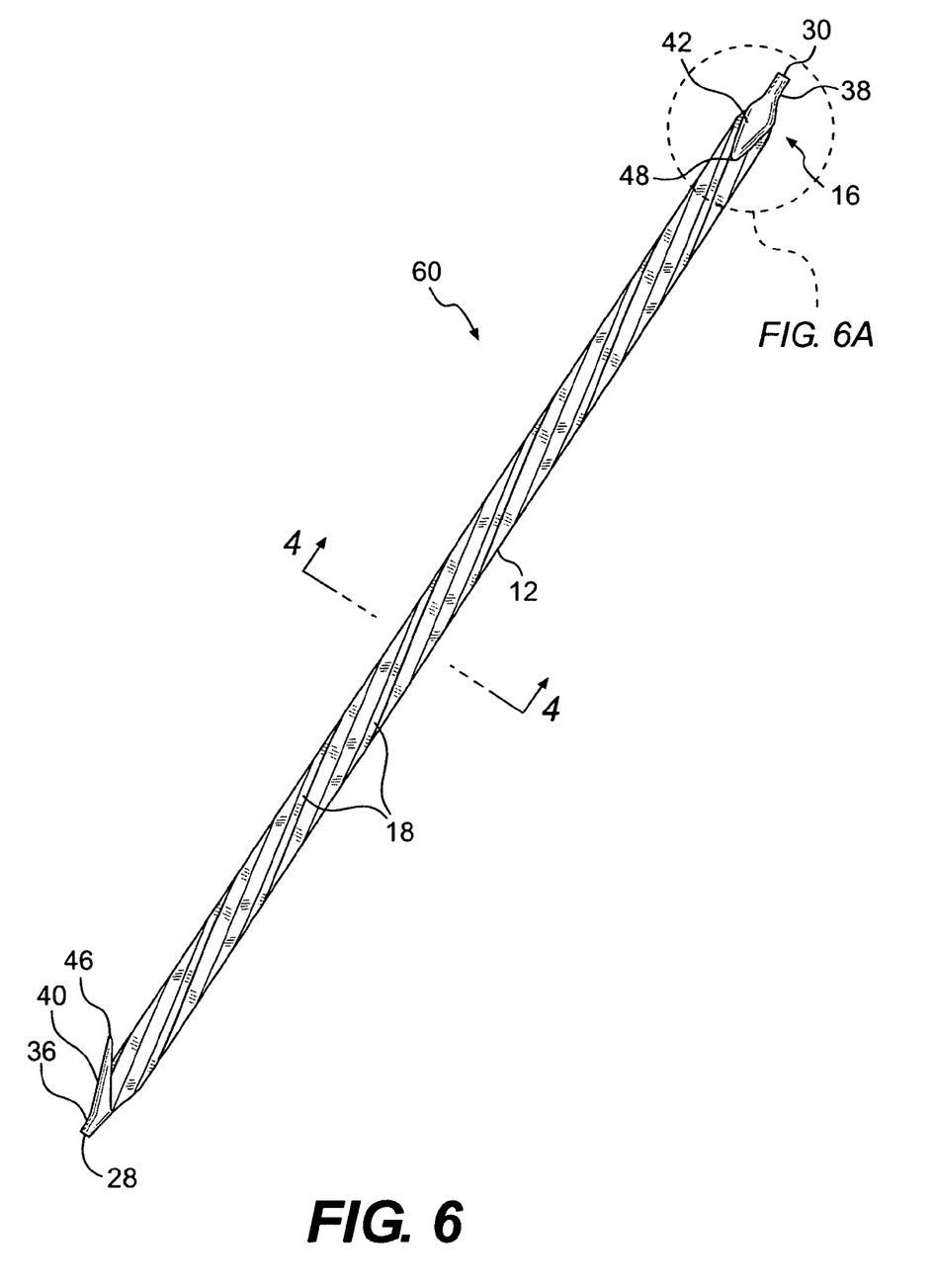
FIG. 6 is a perspective view of a second embodiment of the stent of the present invention, showing an alternative construction for the wings disposed thereon.

Generally cantilevered securement barbs 40, 42 extend outwardly from the tip portions 36, 38 and are angled relative to the central, longitudinal axis 44 of the stent 10. Preferably, the securement barbs 40, 42 are circumferentially positioned such that their tips 46, 48 are longitudinally aligned with each other, as illustrated in FIG. 1. Alternatively, they may be circumferentially offset with respect to each other, as illustrated in FIG. 6, for example.

Figure 2:
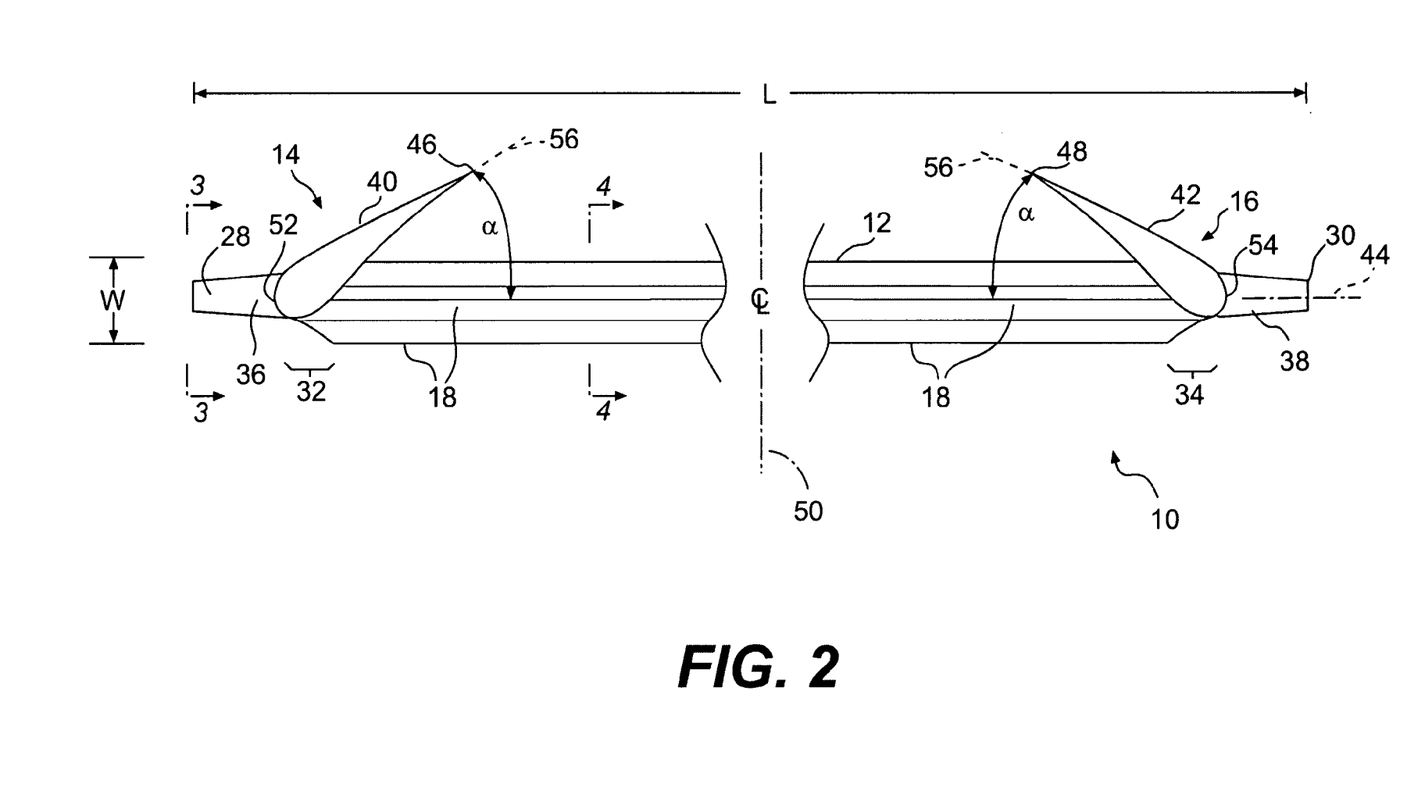
FIG. 2 is an enlarged side view of the embodiment of the stent illustrated in FIG. 1.

As illustrated in FIGS. 1 and 2, the securement barbs 40, 42 are cantilevered and angled in opposite directions. In other words, the tips 46 and 48 of the securement barbs 40, 42 are each positioned longitudinally closer to the longitudinal center 50 of the stent 10 than their respective barb roots 52, 54. This gives each of the ends 14, 16 of the stent 10 a generally half-arrowhead profile, as illustrated in FIG. 2, with the half-arrowheads facing outwardly and away from each other.

Preferably, the securement barbs 40, 42 form an angle α between a line 56 extending along the circumferential center of the radially outer surfaces of each of the securement barbs 40, 42 and the central, longitudinal axis 44 that is less than or equal to about 90°. Preferably, the angle of α is less than or equal to about 75°, with an angle of about 65° being most preferred. Preferably, the angle α is the same at both ends 14, 16 of the stent 10. While the angle of α is preferably about 65°, it is contemplated that the angle α could be greater or smaller, depending on the surgeon's specific needs.

It is believed that the stent 10 will resist migration in the biliary or pancreatic duct if the tips 46, 48 of the securement barbs 40, 42 are disposed at least slightly toward the centerline 50 of the stent 10. Not only does this arrangement ensure that the stent 10 will remain securely emplaced with the biliary or pancreatic duct, but angling the securement barbs 40, 42 in this manner facilitates placement within a patient, because the barbs 40, 42 may be folded against the central portion 12 when the stent 10 is positioned in the biliary or pancreatic ducts using a cannula.

If the securement barbs 40, 42 were disposed such that their tips 46, 48 were disposed at an angle α of greater than 90°, the tips 46, 48 are believed to present a danger of perforating the biliary or pancreatic ducts when the stent 10 is positioned therein. It is, of course, believed possible to manufacture a stent 10 where the angle α is greater than 90° and such a stent is intended to be encompassed hereby.

Next, with respect to the angle α, it is believed that an angle between about 60° and 90° is best to prevent (or at least minimize) migration of the stent 10 once positioned in the biliary or pancreatic duct. If the angle α is reduced to less than 60°, it is believed that securement barbs 40, 42 will likely collapse against the main portion 12 of the stent 10 and, thereby, permit the stent 10 to migrate within the biliary or pancreatic duct.

With an angle α between 60° and 90°, the angle is such that the securement barbs 40, 42 can be compressed against the main portion 12 so as to be relatively flush against the radially outer edges 22 of the wings 18 as the stent 10 is being advanced along an implantation cannula used to implant the stent 10. Upon ejection of the stent 10 from the insertion cannula, the securement barbs 40, 42 flex radially outwardly due to their inherent flexural resiliency to securely retain the stent 10 in the patient's body.

The stent 10 preferably is symmetric with respect to a plane passing through its longitudinal center 50, perpendicularly to the central, longitudinal axis 44. Of course, as would be appreciated by those skilled in the art, symmetry is not required to practice the invention. Specifically, it is contemplated that the stent 10 may not be symmetrical about the plane disposed perpendicularly to the longitudinal axis 44. For example, in one embodiment, it is contemplated there may be only one securement barb 40, 42 at one end of the stent 10, rather than a securement barb 40, 42 at each end. Similarly, only one end may include a conically tapered tip portion 36, 38.

Figure 3:
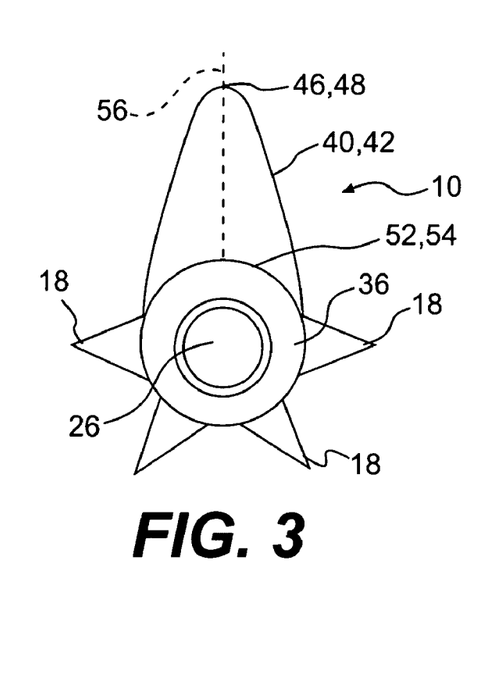
FIG. 3 is an end view of the embodiment of the stent illustrated in FIG. 1, the view being taken from the line 3—3 in FIG. 1.

As illustrated in FIGS. 3 and 4, at their barb roots 52, 54, the securement barbs 40, 42 wrap circumferentially approximately half way around the stent 10, i.e., from one side to the other. Furthermore, as shown in FIG. 3, the side-to-side width of the securement barbs 40, 42 decreases from the barb roots 52, 54 to the barb tips 46, 48, which gives the securement barbs 40, 42 a somewhat teardrop or raindrop profile when the stent 10 is viewed end-on.

As illustrated in FIG. 3, the barb tips 46, 48 are preferably rounded, as viewed end-on. A blunted or rounded tip 46, 48, minimizes the possibility that the barb tips 46, 48 will perforate the biliary or pancreatic duct. Moreover, a blunted or rounded tip 46, 48 assures that stent 10 will not irritate the ductal tissue. Of course, as would be appreciated by those skilled in the art, the tips 46, 48 may have any of a number of shapes without departing from the scope of the invention.

During manufacture, it is contemplated that a length of Pellethane™ (a biocompatible thermoplastic polyurethane elastomer available from Dow Corning and that has been approved by the Food and Drug Administration for implantation) is extruded through an extrusion die having an extrusion opening configured to give the stent 10 the desired cross-sectional configuration when the Pellethane™ has cooled and rigidified.

The extrusion apparatus has a longitudinally extending pin that protrudes through the extrusion opening in the extrusion die to form the guidewire lumen 26. After the Pellethane™ has cooled sufficiently to work with it, i.e., for the wings 18 to retain their shape when the extrusion is handled, the extrusion is cut into lengths corresponding to the length of the final biliary stent product. Then, the transition regions 32, 34 are formed, which preferably taper substantially to a somewhat blunted point.

The tip portions 36, 38, which include the cantilevered securement barbs 40, 42, are manufactured separately. Then, the manufacture of the stent 10 is completed by attaching the tip portions 36, 38 to the transition regions 32, 34.

Figure 6A:
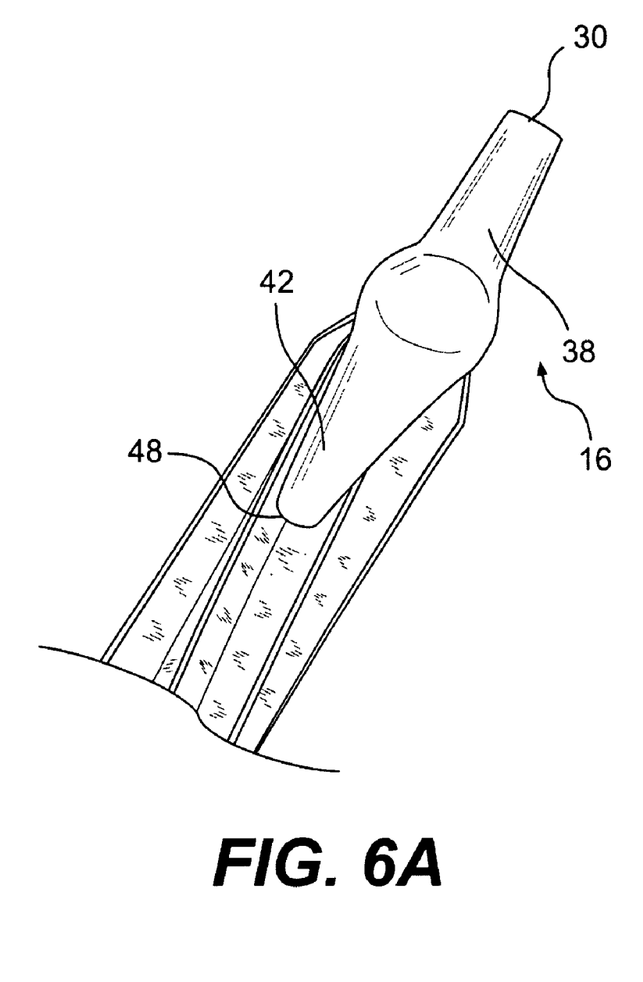
FIG. 6A is an enlarged view of one end of the stent depicted in FIG. 6.
Figure 7:
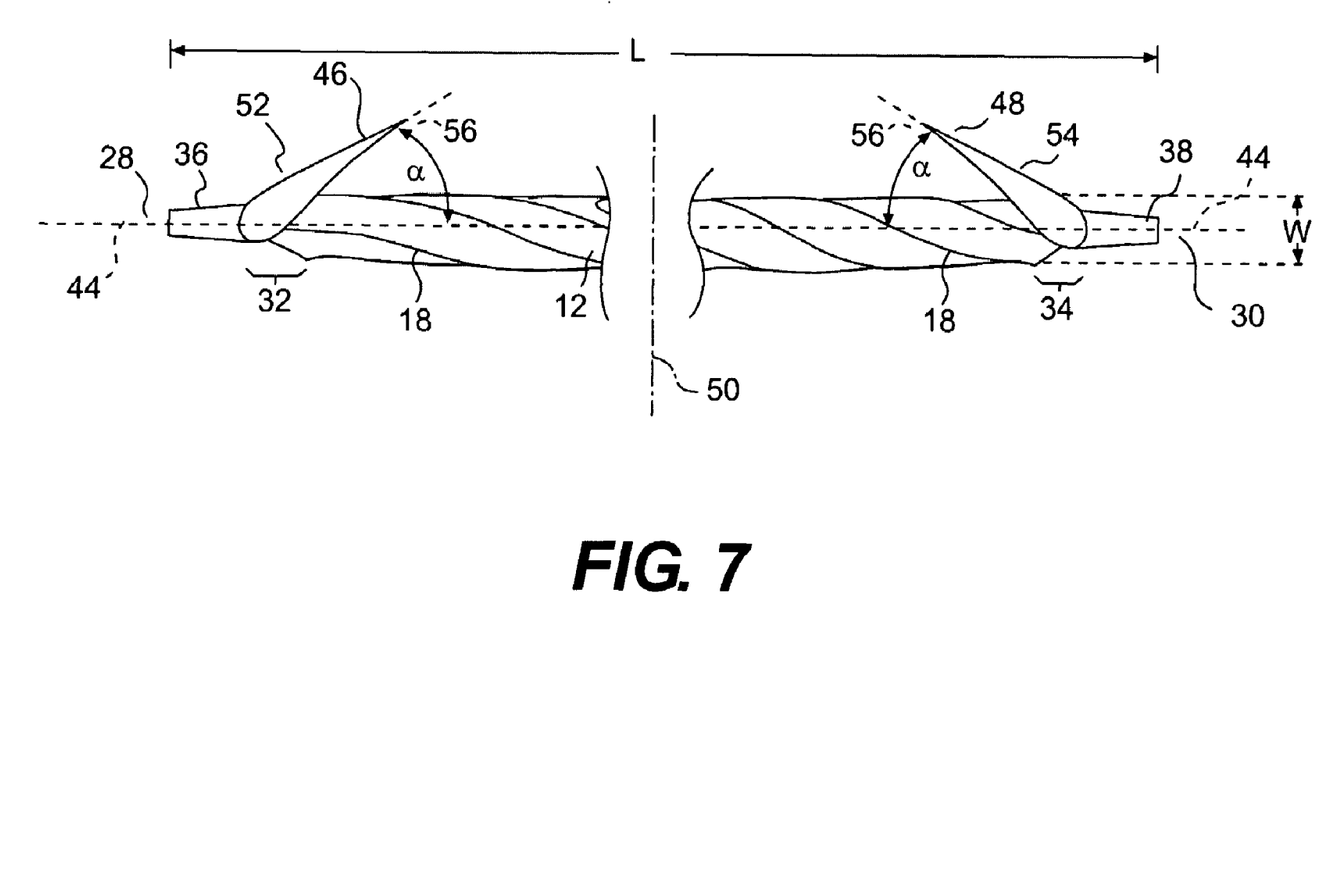
FIG. 7 is an enlarged side view of the embodiment of the stent illustrated in FIG. 6.

A second embodiment 60 of a stent according to the invention is illustrated in FIGS. 6, 6A, and 7. The stent 60 differs from the first embodiment in that the wings 18 are helically configured. This helical configuration is obtained simply by rotating the extrusion die as the Pellethane™ is extruded. Because the parts and components of the stent 60 are otherwise identical to the parts and components of the stent 10 shown in FIGS. 1–5, identical reference numbers are used to describe both embodiments and the second embodiment is not described further herein.

Figure 8:
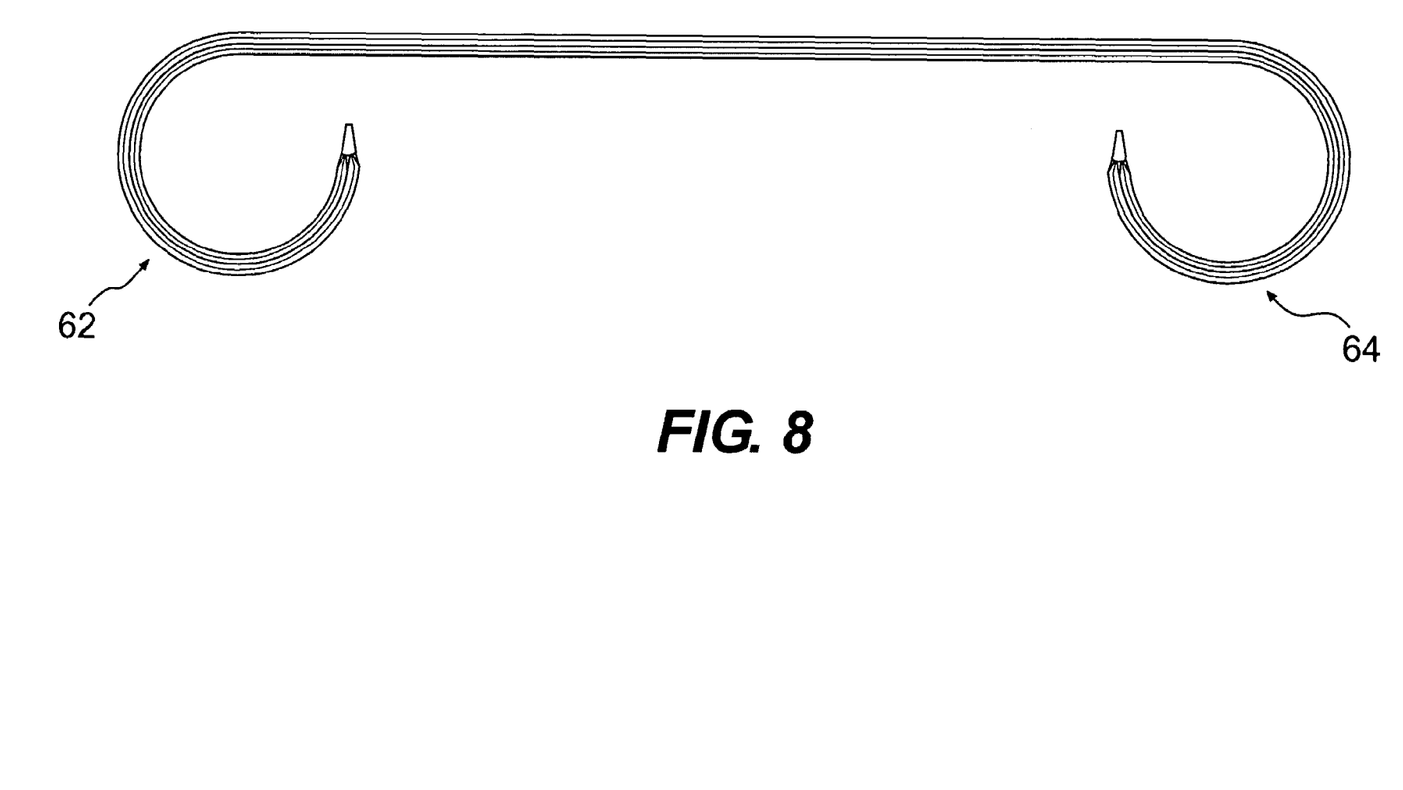
FIG. 8 is a top view of another embodiment of the stent illustrated in FIG. 1, showing an alternative arrangement of the ends thereof.

As illustrated in FIG. 8, the stent 10 or 60 according to the invention may include a pig-tail configuration 62, 64, in which one or both ends of the stent 10, 60 is/are curled to a desired extent. This configuration may be used instead of the securement barbs 40, 42.

In the embodiment illustrated in FIG. 8, the pig tails 62, 64 are not shown with the securement barbs 40, 42. Of course, as would be appreciated by those skilled in the art, the pig tails 62, 64 may be used in conjunction with the securement barbs 40, 42. When used together, the pig tails 62, 64 increase the engagement pressure (the frictional engagement) between the stent 10, 60 and the walls of the biliary or pancreatic duct.

The embodiments of the stent 10, 60 of the present invention are described with securement barbs 40, 42 disposed at the tip portions 36, 38. Of course, as would be appreciated by those skilled in the art, the barbs 40, 42 may be positioned between the tip portions 36, 38 at locations on central portion 12. Moreover, while only two barbs 40, 42 are discussed, a plurality of barbs 40, 42 may be employed to secure the stent 10, 60 in the biliary or pancreatic duct.

Preferably, in order to maximize the benefit of a pig-tail configuration, the securement barbs 40, 42 should be located such that the resiliency of the stent 10, 60 biases the securement barbs 40, 42 against the walls of the biliary or pancreatic duct.

As discussed, Pellethane™ is the preferred material for the manufacture of the stent 10, 60 because of its flexural characteristics. Moreover, Pellethane™ is preferred because it has been approved by the Food and Drug Administration for implantation in human patients. As would be appreciated by those skilled in the art, however, other materials may be used instead of Pellethane.™

While the invention has been described in connection with what is presently deemed to be the most practical and preferred embodiments, it should be understood that the invention is not limited to the disclosed embodiments. Rather, the invention is intended to cover various modifications and equivalent arrangements included within the spirit and scope of the following claims.

What is claimed is:

1. A stent, comprising:
   a body with a predetermined length defining a longitudinal axis and two ends;
   a plurality of smooth-surfaced wings angularly spaced around the body and extending radially outwardly from the body and extending longitudinally along substantially the entire length thereof, wherein channels are formed between adjacent wings, each channel extending substantially the entire length of the body and defining a fluid flow passage;
   at least two securement barbs, at least one disposed at each end of the body, each barb having a barb root and a barb tip, the barb root securing the securement barb to the body, the securement barb extending generally radially outwardly from the body in cantilevered fashion from the barb root to the barb tip, the securement barb being angled relative to the longitudinal axis with the barb root being located nearer to the end of the body than the barb tip; and
   a conically tapered tip portion disposed at each end of the body and distal to each barb.

2. The stent according to claim 1, wherein each of the at least two securement barbs extend radially outward from each end of the body such that the tips of each of the securement barbs are located nearer to a center of the body than the barb roots.

3. The stent according to claim 2, wherein the stent is generally symmetric about a plane passing through a longitudinal center thereof and normal to the longitudinal axis of the body.

4. The stent according to claim 1, wherein each of the at least two securement barbs is disposed at a barb angle equal to or less than 90° relative to the longitudinal axis of the body.

5. The stent according to claim 4, wherein the barb angle is equal to or less than about 75°.

6. The stent according to claim 5, wherein the angle is about 65°.

7. The stent according to claim 4, wherein the angle is between 60° to 90°, inclusive.

8. The stent according to claim 1, wherein each of the at least two securement barbs extend from a respective conically tapered tip portion.

9. The stent according to claim 1, wherein each of the conically tapered tip portions extend from a transition region on the body, the transition region being located where the radial height of the wings decreases toward the end thereof.

10. The stent according to claim 1, wherein the wings are disposed substantially parallel to one another.

11. The stent according to claim 10, wherein there are three or more wings.

12. The stent according to claim 10, wherein there are six wings.

13. The stent according to claim 10, wherein the wings extend linearly along the body.

14. The stent according to claim 10, wherein the wings extend helically along the body.

15. The stent according to claim 1, wherein the wings each have a wing root and a wing edge and taper in width from the wing root to the wing edge thereof.

16. The stent according to claim 1, wherein the wings each have a wing root and a wing edge with essentially a constant thickness from the wing root to the wing edge thereof.

17. The stent according to claim 1, wherein the wings each have a wing root and a wing edge and the wing edges are rounded or blunted slightly.

18. The stent according to claim 1, wherein the body and the securement barbs comprise thermoplastic polyurethane elastomers.

19. The stent according to claim 1, wherein at least one of the ends of the body has a pigtail configuration.

20. The stent according to claim 1, wherein the stent is a biliary stent.

21. The stent according to claim 1, wherein the stent is a venous stent.

22. The stent according to claim 1, wherein the stent is an arterial stent.

23. A stent, comprising:
   a body with a predetermined length defining a longitudinal axis and two ends;
   a plurality of smooth-surfaced wings angularly spaced around the body and extending radially outwardly from the body and extending longitudinally along substantially the entire length thereof, wherein channels are formed between adjacent wings, each channel extending substantially the entire length of the body and defining a fluid flow passage;
   at least two securement barbs, at least one disposed at each end of the body, each barb having a barb root and a barb tip, the barb root securing the securement barb to the body, the securement extending generally radially outwardly from the body in cantilevered fashion from the barb root to the barb tip, the securement barb being angled relative to the longitudinal axis with the barb root being located nearer to the end of the body than the barb tip;
   a conically tapered tip portion disposed at each end of the body and distal to each barb; and
   a lumen defined within the body, the lumen extending through the body between the two ends thereof and being constructed and arranged to accommodate a guide wire therein.

24. The stent according to claim 1, wherein each of the securement barbs tapers in width from the barb root to the barb tip thereof.

25. The stent according to claim 18, wherein the barb root extends circumferentially approximately half way around the body.

26. The stent according to claim 25, wherein each of the securement barbs has a generally teardrop shape.

27. A stent, comprising:
- a body with a predetermined length defining a longitudinal axis and two ends, with a conical tapered tip portion being disposed at each end of the body;
- a lumen defined within the body, the lumen extending through the body between the two ends thereof and being constructed and arranged to accommodate a guide wire therein;
- a plurality of smooth-surfaced wings angularly spaced around the body and extending radially outwardly from the body and extending longitudinally along substantially the entire length thereof, wherein channels are formed between adjacent wings, each channel extending substantially the entire length of the body and defining a fluid flow passage; and
- a securement barb disposed adjacent to each end of the body and extending from each of the conical tip portions, each securement barb having 1) a barb root securing the securement barb to the body and 2) a barb tip, with the securement barbs each tapering in width from the barb root to the barb tip thereof such that each securement barb has a generally teardrop shape, each securement barb extending generally radially outwardly from the body in cantilevered fashion from the barb root to the barb tip and being disposed at an angle of less than or equal to about 90° relative to the longitudinal axis of the body, the securement barbs being angled in opposite directions with respect to each other, with the barb roots being located nearer to the ends of the body than the barb tips.

28. The stent according to claim 27, wherein the angle of each securement barb is less than or equal to about 75° relative to the longitudinal axis of the body.

29. The stent according to claim 27, wherein the angle of each securement barb is about 65° relative to the longitudinal axis of the body.

30. The stent according to claim 27, wherein the wings are disposed substantially parallel to one another.

31. The stent according to claim 27, wherein the wings extend linearly along the body.

32. The stent according to claim 27, wherein the wings extend helically along the body.

33. The stent according to claim 27, wherein the body and the wings comprise thermoplastic polyurethane elastomers.

34. The stent according to claim 27, wherein the stent is a biliary stent.

35. The stent according to claim 27, wherein the stent is a venous stent.

36. The stent according to claim 27, wherein the stent is an arterial stent.

* * * * *